Figure 1:
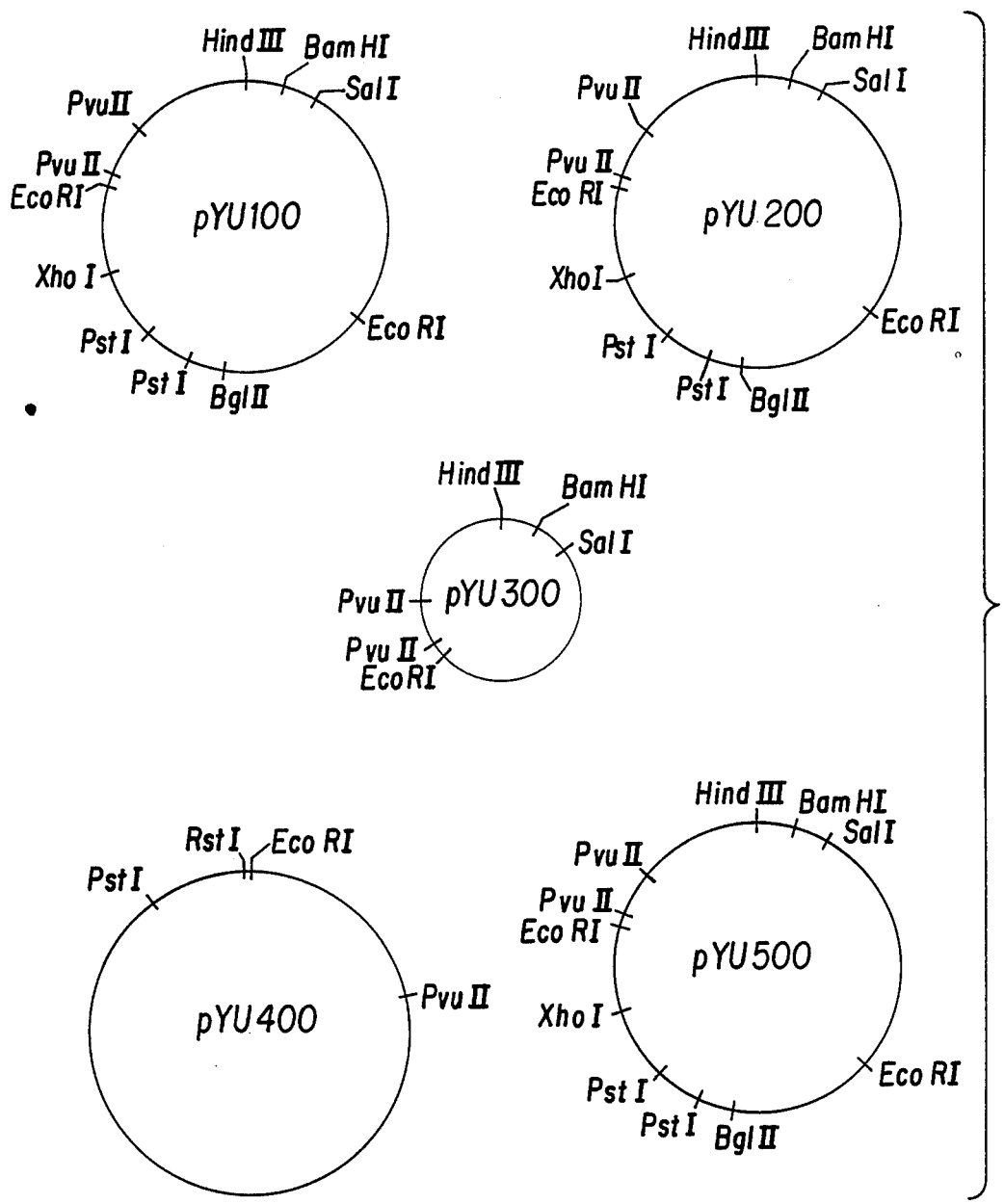

| United States Patent [19] | [11] Patent Number: 4,945,058 |
|---|---|
| Yanai et al. | [45] Date of Patent: Jul. 31, 1990 |

[54] PLASMID WITH WIDE HOST RANGE AND PROCESS OF PRODUCING L. THREONINE USING THE SAME

[76] Inventors: Akira Yanai, 4-21, 2-chome, Tsunishi, Kamakura, Japan, 248; Yoshizumi Ueda, 81-K, 1-Chome, Ikegamidai, Midori-ku, Nagoya, Japan, 458

[21] Appl. No.: 919,993

[22] Filed: Oct. 17, 1986

[30] Foreign Application Priority Data

Oct. 18, 1985 [JP] Japan .................................. 60-230993
Oct. 18, 1985 [JP] Japan .................................. 60-230996

[51] Int. Cl.$^5$ ........................ C12N 1/20; C12N 15/00; C12P 13/08
[52] U.S. Cl. ................................ 435/252.3; 435/115; 435/172.3; 435/320; 935/29; 935/60; 935/72
[58] Field of Search ....................... 435/68, 70, 71, 91, 435/115, 172.1, 172.3, 253, 320, 252.3, 252.31–252.34, 69.1, 71.2; 935/29, 60, 72, 73

[56] References Cited

U.S. PATENT DOCUMENTS

4,321,325  3/1982  Debabov et al. ................... 435/115

OTHER PUBLICATIONS

*Supplement to Index Bergeyana*, Gibbons et al, 1981, Williams & Wilkins, Baltimore, p. 215.
Cossart et al; Molec. Gen. Geneti 175: 39 (1979).
American Type Culture Collection Catalogue of Strains I, 15th Edition, 1982, American Type Culture Collection, Rockville, Md., p. 166.
Vymola et al; Chem. Abstr. 91: 16508m (1979).
Urbaskova et al; Chem. Abstr. 88: 71342r (1978).
Barbuti et al; Chem. Abstr. 98: 31073d (1983).
Desai et al; Chem. Abstr. 95: 162895j (1981).
*Bergey's Manual of Determinative Bacteriology*, Buchanan et al (ed.), 1974, Williams & Wilkins Co., Baltimore, pp. 327–329.
Katinka et al; Proc. Natl. Acad. Sci. USA 77: 5730 (1980).
Cossart et al; Nucleic Acids. Res. 9: 339 (1981).
Chabbert et al: J. Antimicrob. Chemother, 3 (Suppl. C), 25 (1977).
Bradley et al; J. Gen. Microbiol. 126: 389 (1981).
*Molecular Cloning, A Laboratory Manual*, Maniatis et al, 1982, Cold Spring Harbor Laboratory, Cold Spring Harbor, N.Y., pp. 86–96.
*Advanced Bacterial Genetics*, Davis et al, Cold Spring Harbor Laboratory, Cold Spring Harbor, N.Y., pp. 138, 139, and 227–230.
Birnboim et al; Nucleic Acids Res. 7: 1513 (1979).
Tietze et al; J. Hyg., Camb. 90: 475 (1983).
Goodenough, U., Genetics, (1984), pp. 400, 401, and 425–431.
Bergey's Manual of Systematic Bacteriology, vol. 1, (1984), pp. 12–13 and 491–496.
Brenner et al., International Journal of Systematic Bacteriology, Apr. 1978, vol. 28, No. 2, pp. 269–282.
Stent, G. S., Molecular Genetics, (1971), pp. 252, 253 and 256–259.
Shigesada, K., Cell Technology, vol. 2, No. 3, 1983, English Translation.
Saito, H., Preparation of Bacterial and Phage DNA, English Translation.
Vymola, M., Journal of Hygiene, Epidemiology, Microbiology and Immunology 2, 1978, No. 3, 382–384. "R Plasmids in . . . ".
Desai, B. R., Indian J Med Res 74, Aug. 1981, pp. 192–195, "Transferable Drug Resistance in Proteus Species".
Stanier, R. Y. et al., The Microbial World, (1970), pp. 511–514 and 541.

*Primary Examiner*—James Martinell
*Attorney, Agent, or Firm*—Pennie & Edmonds

[57] ABSTRACT

This invention provides a plasmid with a wide host range, which can replicate in microorganisms belonging to the family Enterobacteriaceae. These plasmids may be used to clone the genes repsonsible for the fermentative production of various useful biochemicals. The recombinant plasmids containing these genes can be used to transform bacteria so that the fermentative production of the biochemical is enhanced.

11 Claims, 5 Drawing Sheets

4,945,058

PLASMID WITH WIDE HOST RANGE AND PROCESS OF PRODUCING L. THREONINE USING THE SAME

1. INTRODUCTION

This invention relates to plasmids having a wide host range which can be used in genetic engineering techniques, and to processes for the fermentative production of various biochemically products using the plasmids of the invention. The invention is demonstrated herein by way of examples in which essential amino acids such as L-lysine and L-threonine are fermentatively produced using the plasmids having a wide host-range.

2. BACKGROUND OF THE INVENTION

The family Enterobacteriaceae are known to include many genera of bacteria which produce biochemically useful products such as the L-histine-producing bacterium, *Serratia marcescens* ATCC 31026; L-threonine-producing bacteria, *Providencia rettgeri* ATCC 21118, *Proteus vulgaris* ATCC 21117, *Klebsiella pneumoniae* ATCC 21316 and *Escherichia coli* ATCC 21278; L-valine-producing bacterium, *Citrobacter freundii* ATCC 11102; 2-ketogluconic acid-producing bacterium, *Erwinia herbicola* ATCC 21998; polynucleotide phosphorylase-producing bacterium, *Proteus mirabilis* ATCC 21635; and *Enterobacter cloacae* ATCC 15337 having insecticidal property against Lepidoptera. The fermentative production of each product involves complex biochemical pathways controlled by multiple genes and gene products. The fermentative products are produced in relatively low amounts. It would be advantageous if the fermentative production of these useful biochemicals could be enhanced.

3. SUMMARY OF THE INVENTION

This invention provides a plasmid with a wide host range, which can replicate in microorganisms belonging to the family Enterobacteriaceae. These plasmids may be used to clone the genes responsible for the fermentative production of various useful biochemicals. The recombinant plasmids containing these genes can be used to transform bacteria so that the fermentative production of the biochemical is enhanced.

The present invention is based, in part, upon the discovery and isolation of plasmids from *Providencia rettgeri*, which plasmids can replicate not only in *Escherichia coli*, but also in the bacteria belonging to the genera Citrobacter, Enterobacter, Erwinia, Klebsiella, Providencia and Salmonella, and which have a drug-resistant selective marker which can be conveniently used in genetic engineering procedures.

The invention is demonstrated by way of examples in which the fermentative productivity of L-lysine and L-threonine is increased by utilizing a transformant obtained by a process comprising cloning the genes responsible for the fermentative production of L-lysine and L-threonine using the above wide host-range plasmids. Accordingly, recombinant plasmids containing the genes responsible for the fermentative production of L-lysine and L-threonine, respectively, are constructed and used to transform bacterial hosts belonging to the genus Providencia or Escherichia. The transformants which produce high levels of L-lysine or L-threonine, respectively are cultured.

4. BRIEF DESCRIPTION OF THE FIGURES

FIG. 1 diagrammatically represents the restriction maps of wide host range plasmids pYU100, pYU200, pYU300, pYU400 and pYU500.

Figure 2:
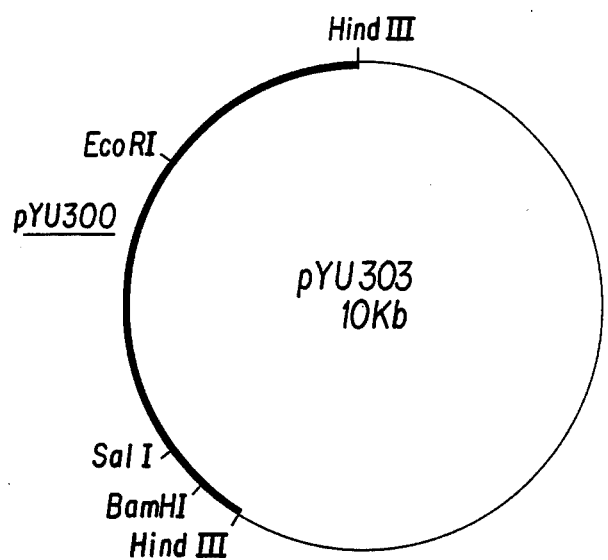

FIG. 2 diagrammatically represents the restriction map of recombinant plasmid pYU303 which contains a 6 kb DNA insert that contains the gene coding for diaminopimelic acid decarboxylase, an enzyme which converts diaminopimelic acid to lysine.

Figure 3:
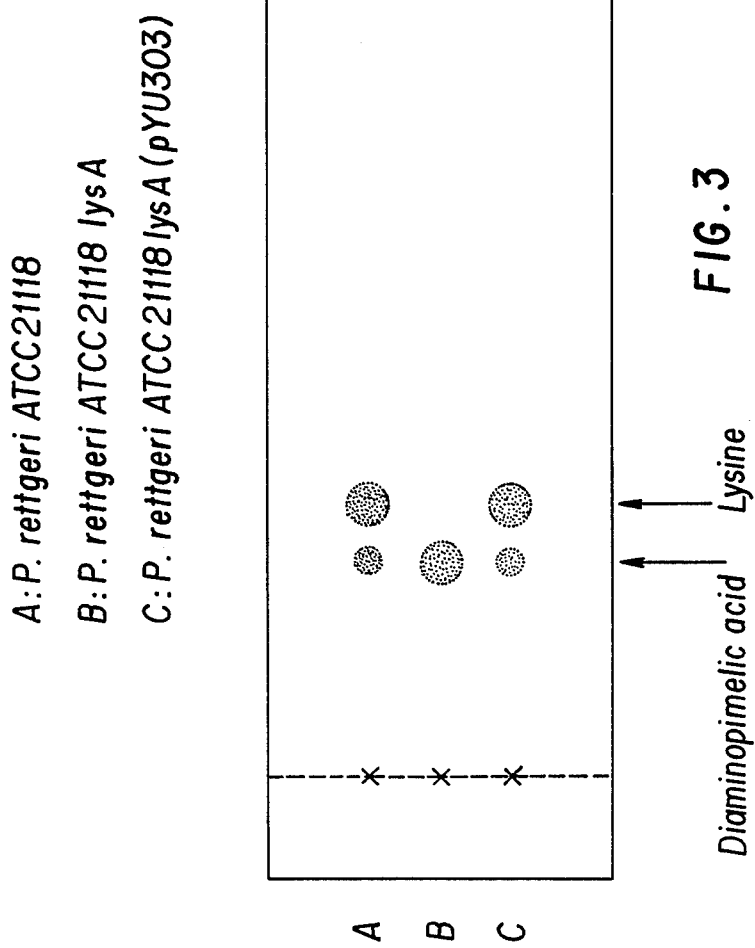

FIG. 3 shows the results of thin layer chromatography of media containing diaminopimelic acid after incubation with the bacteria indicated. Diaminopimelic acid decarboxylase activity was detected in *P. rettgeri* ATCC 21118 and in the *P. rettgeri* ATCC 21118 Lys⁻ (pYU303) transformant which converted the diaminopimelic acid substrate to lysine. Such activity was not detected in the non-transformed auxotrophic mutant, *P. rettgeri* ATCC 21118 Lys⁻.

Figure 4:
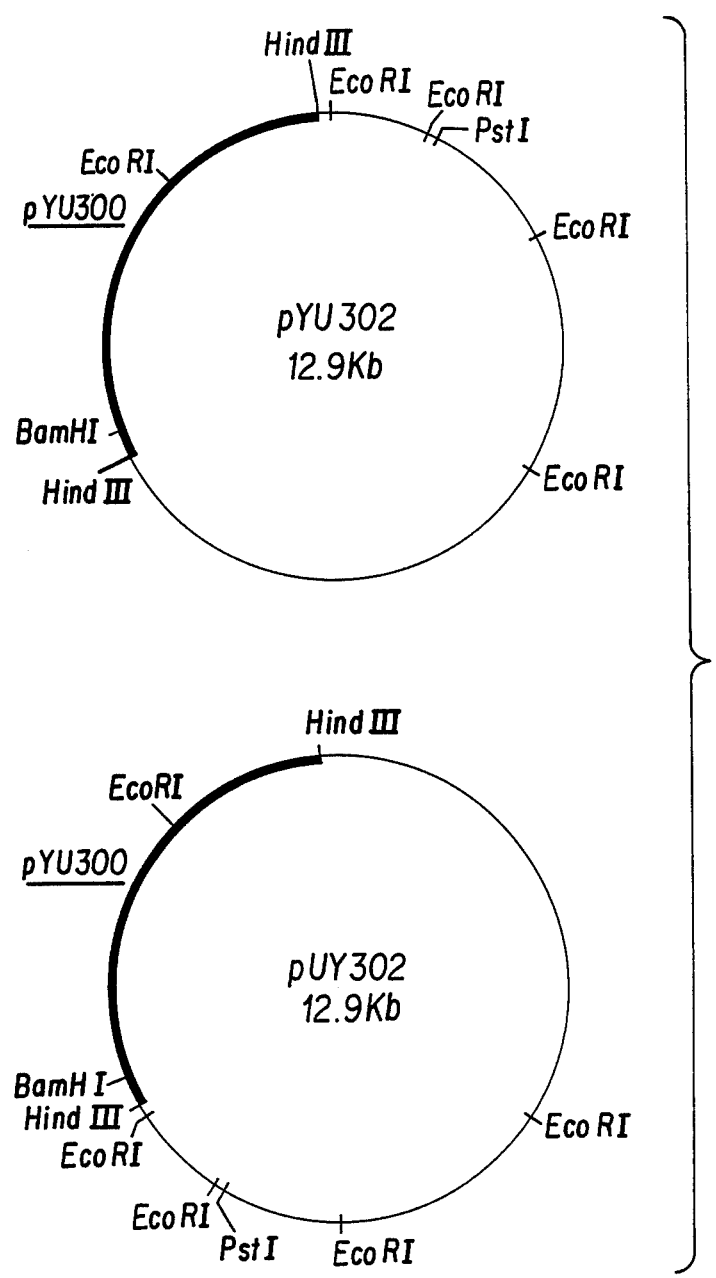

FIG. 4 diagrammatically represents the restriction map of recombinant plasmids pYU302 and pUY302. These recombinant plasmids comprise pYU300 containing in its HindIII site an 8.7 kb DNA insert that codes for an enzyme responsible for the fermentative production of L-threonine. Each plasmid contains the 8.7 kb DNA in an opposite orientation.

Figure 5:
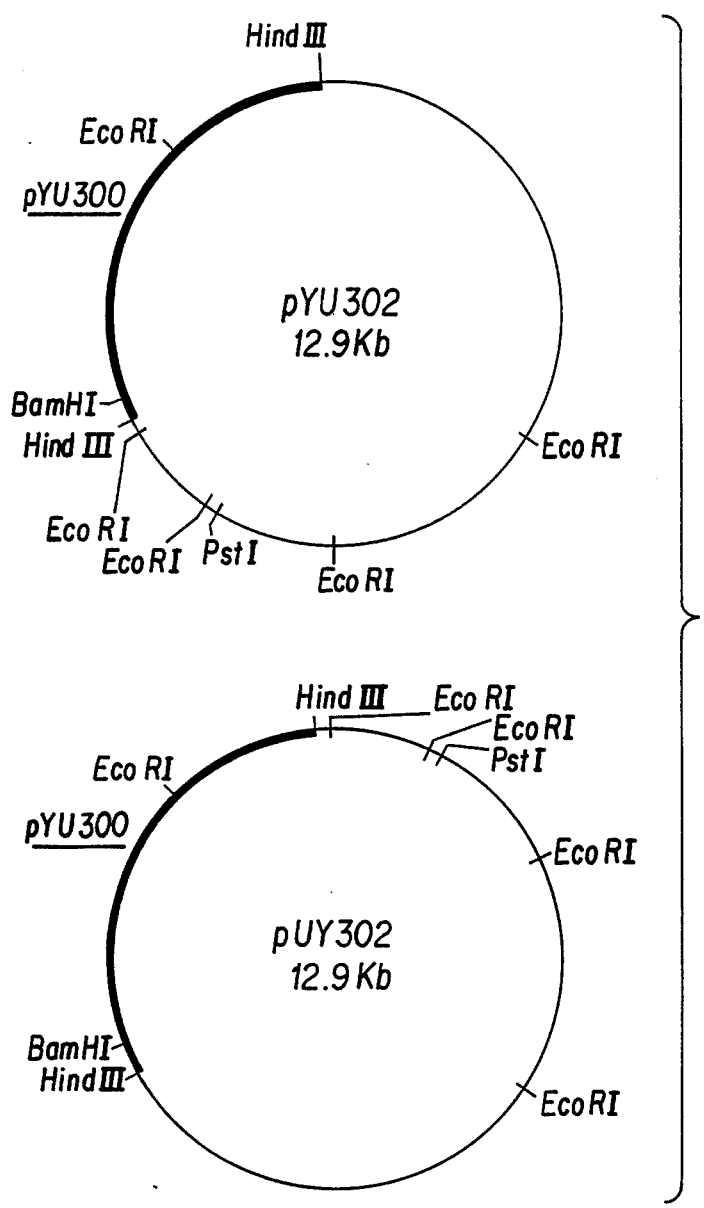

FIG. 5 diagrammatically represents the restriction maps of recombinant plasmid pYU310 and pUY310. These recombinant plasmids comprise pYU300 containing in its HindIII site an 8.7 kb DNA insert that codes for an enzyme responsible for the fermentative production of L-threonine. Each plasmid contains the 8.7 kb DNA in an opposite orientation.

5. DETAILED DESCRIPTION OF THE PREFERRED EMBODIMENTS

The subsections below describe the construction of plasmids having a wide host range, which can be used to enhance the fermentative production of useful biochemicals.

5.1. PRODUCTION OF PLASMIDS WITH A WIDE HOST RANGE

The plasmids with wide host range of the present invention may be extracted from *Providencia rettgeri* (hereinafter referred to as *P. rettgeri*) ATCC 25932, ATCC 9919 or ATCC 29944. That is, the donor of the parent plasmid may be *P. rettgeri* ATCC 25932, ATCC 9919, or ATCC 29944. Replication and extraction of the plasmid may be conducted by conventional methods such as those described, for example, in "Molecular Cloning, A Laboratory Manual", 1982, Maniatis et al., Cold Spring Harbor Laboratory, New York, pp. 86-96; and Birnboim and J. Dory, 1979, Nucleic Acid Res. 7: 1513-1523. In this case, although not mandatory, the yield of the plasmid may be increased by conducting the bacteriolysis step at 30° to 60° C. for 20 to 60 minutes.

The plasmid fraction extracted from *P. rettgeri* comprises a mixture of plasmids each of a different size. In order to select those plasmids which have a wide host range, the mixture of plasmids extracted from *P. rettgeri* are used to transform a second host, preferably one with well-studied properties such as *Escherichia coli* (*E. coli*). Accordingly, *E. coli* can be transformed with the mixture of *P. rettgeri* plasmids by conventional methods using appropriate drug resistance selective markers (see for example, Katsuya Shigesada, 1983, Cell Technology 2: 615-626). In order to obtain a purified plasmid with a wide host range that comprises a homogeneous population each of the same size, it may be necessary to repeat the transformation of *E. coli* using serially diluted plasmid solutions to decrease the number of plasmids contained in a transformant; thus, the transformation can be repeated until a single plasmid is contained in the transformant. Plasmids can be purified from these transformants using conventional plasmid-detecting methods as described above.

The bacteria belonging to the genus Citrobacter, Enterobacter, Erwinia, Escherichia, Klebsiella, Providencia or Salmonella may be transformed with the plasmids of the present invention by a conventional method as described, for example, in Katsuya Shigesada, 1983, Cell Technology 2: 616–626; that is, making the bacteria competent by using calcium ion or rubidium ion. The screening of the transformants may be conducted by utilizing the drug resistance thereof.

Although the invention is not limited thereto, each plasmid may be conveniently replicated in *E. coli* of which properties have been well studied. In some cases, to obtain a higher efficiency in transformation, it is preferred to preliminarily replicate the plasmid in a bacterium to be transformed to reduce the host-controlled modification.

The plasmid may be extracted and purified by a conventional method as described, for example, in "Molecular Cloning, A Laboratory Manual," 1982, Maniatis et al., ed, Cold Spring Harbor Laboratory, New York pp. 86–96; Katsuya Shigesada 1983, Cell Technology 2: 616–626. Although not mandatory, the yield may be increased if the bacteriolysis step is conducted at 30° to 65° C. for 20 to 60 minutes.

The novel plasmids thus obtained may find wide range of use for example, as shuttle vectors in genetic engineering techniques which can utilize *E. coli* as a host whose genetic properties are well known.

5.2. INCREASED FERMENTATIVE PRODUCTION OF GENE PRODUCTS USING THE PLASMIDS HAVING WIDE HOST RANGE

A number of bacteria belonging to the family Enterobacteriaceae produce biochemically useful products, examples of which are described in Section 2 above. These bacteria necessarily contain the genes responsible for such fermentative production. In accordance with the invention, these bacteria are used as the source of the genes to be cloned and expressed using an auxotrophy complementation method described herein. Briefly, the auxotrophy complementation method of this embodiment of the invention involves the following steps: (a) chromosomal DNA is extracted from a bacteria which fermentatively produces the biochemical product of interest; (b) the chromosomal DNA is fragmented into different segments; (c) the chromosomal DNA fragments are "shotgun cloned" by ligation into the plasmid vectors having a wide host range described in Section 5.1. to form a mixed population of recombinant plasmids having a wide host range, some of which contain the genetic information responsible for the fermentative process; (d) the recombinant plasmids are used to transform an auxotrophic mutant bacterium host which requires the biochemical product of interest for growth; (e) transformants are then screened for rescue of the gene product in order to confirm the presence of the gene in the recombinant plasmid; and (f) the recombinant plasmid may then be used to transform a host cell which fermentatively produces the biochemical product of interest in order to increase the gene copy number and, therefore, to increase fermentative production of the biochemical product of interest by that host.

This embodiment of the invention is described by way of example herein, for the production of L-lysine and L-threonine. For purposes of clarity of description, the method of the invention will be described below in more detail in terms of producing L-threonine. However, the invention is not limited to the production of L-threonine, in that the procedures described may be used to produce any desirable product including but not limited to L-histidine (e.g., produced by Serratia), L-valine (e.g., produced by Citrobacter), 2-ketogluconic acid (e.g., produced by Erwinia), polynucleotide phosphorylase (e.g., produced by Proteus), or the insecticidal factor of *Enterobacteria cloacae*.

The genes responsible for the fermentative production of L-threonine (for example, threonine synthase) may be obtained from a bacterium belonging to the genus Providencia such as, for example, *P. rettgeri* ATCC 21118, but the invention is not limited to the use of this strain and variants such as L-threonine regulatory mutants may be utilized as a source of the gene. The extraction of chromosomal DNA may be accomplished by a conventional method as described, for example, in Hyuga Saito, 1966, Protein, Nucleic Acid, Enzyme, Vol. 11, pp. 446–450. In this case, although not mandatory, the yield of DNA may be increased by conducting the bacteriolysis step at 30° to 65° C. for 20 to 60 minutes.

The previously described plasmids with wide host range derived from *P. rettgeri* may preferably be used as a vector. Although the plasmid may be extracted from *P. rettgeri* ATCC 25932, ATCC 9919, or ATCC 29944, it is most convenient to extract the plasmid pYU300 from *P. rettgeri* ATCC 21118 (pYU300) (FERM BP-1174) which was obtained by transforming *P. rettgeri* ATCC 21118 with a 4.2 kb plasmid, pYU300, extracted from *P. rettgeri* ATCC 25932.

The self-cloning of the gene responsible for the production of L-threonine may be conducted by a shot gun process utilizing L-threonine auxotrophic mutants in the method as described, for example, in Birnboim and J. Dory, 1979, Nucleic Acid Res. 7: 1513-1523. The fragmentation of chromosomal DNA and the cutting of the plasmid may be conducted by a conventional enzymatic reaction using a restriction enzyme such as, for example, HindIII. The ligation of the DNA fragment and the vector may be conducted by a conventional ligation reaction by using an enzyme such as, for example, T4 DNA ligase. The cohesive end of the vector may be subjected to a treatment with alkaline phosphatase as described, for example, in "Advanced Bacterial Genetics, A Manual for Genetic Engineering," 1980, Davis et al., eds., to prevent the self-cyclization of the vector. Making the host competent and the transformation of the host may be conducted by a conventional method as described for example, in Katsuya Shigesada, 1983, Cell Technology 2: 616–626. The screening of the transformants may be conducted utilizing the marker rescue of the L-threonine auxotrophy of the host as an indicator. The efficiency of the screening may be promoted by combining the selection in accordance with the drug resistance of the vector.

The recombinant plasmid may be extracted from the thus obtained transformant as described, for example, in Birnboim and Dory, 1979, Nucleic Acid Res. 7: 1513-1523, and a *P. rettgeri* strain which possesses the fermentative ability to produce L-threonine may be transformed with the recombinant plasmid. The resulting transformant may be selected according to the high fermentative ability to produce L-threonine. The fermentative production of L-threonine may be further promoted by proper selection of the host to be transformed. Such hosts include, but are not limited to auxotrophic mutants, mutants in which feedback inhibition and/or repression of the synthesis system of L-threonine is reduced, mutants in which degradation of L-threonine is reduced, or mutants with a combination of these characters.

By culturing the transformant in a L-threonine fermentation medium, L-threonine may be accumulated in the medium at a high concentration. The medium may be a conventional one containing a carbon source, nitrogen source and inorganic ions, and, if necessary, an amino acid. In the seed culture, it is preferred to apply a selective pressure by adding to the medium the drug against which the plasmid is resistant to prevent the dropout of the plasmids. As the carbon source, glucose, sucrose or the like, or hydrolysate of starch or syrup containing such a sugar may be used. As the nitrogen source, aqueous ammonia solution or ammonium salt may be used. Culturing may be conducted under aerobic condition appropriately adjusting the pH and the temperature of the medium.

The L-threonine accumulated in the medium may be isolated and purified according to a conventional method.

By using the transformants of the present invention, not only is the concentration of the accumulated L-threonine higher than that obtained using the known L-threonine-producing strain of *P. rettgeri*, but also the culturing time can be shortened.

The present invention will now be described in more detail referring to the examples of the present invention.

6. EXAMPLE: PRODUCTION OF PLASMID VECTORS WITH WIDE HOST RANGES

The subsections below describe the production of plasmids (pYU100, pYU200, pYU300, pYU400, and pYU500) which have a wide host range.

6.1. ISOLATION OF PLASMIDS WITH WIDE HOST RANGE

*P. rettgeri* ATCC 25932 aerobically cultured in one liter of L-broth (1% tryptone, 0.5% yeast extract, 1% sodium chloride, pH 7.5) at 37° C. for 16 hours was suspended in 3 ml of 0.5M NaCl, 0.1M EDTA, 50 mM Tris-HCl (pH 8) containing 15 mg of lysozyme hydrochloride, and was incubated at 37° C. for 15 minutes. The suspension was then frozen and thawed, and 25 ml of 0.1M Tris-HCl (pH 9), 1% SDS, 0.1M NaCl was added to the suspension and the mixture was incubated at 60° C. for 20 minutes to lyse the cells. The cell lysate was centrifuged at 30,000 rpm (100,000×g) for 30 minutes. To the supernatant, was added 10 µl of 10 mg/ml RNase A, and the mixture was incubated at 37° C. for 1 hour. After the incubation, the mixture was subjected to phenol extraction and then ethanol precipitation to obtain crude DNA. The crude DNA was subjected to Biogel column chromatography and then density gradient centrifugation in cesium chloride-ethidium bromide as described in "Molecular Cloning, A Laboratory Manual", 1982, Maniatis et al., ed., Cold Spring Harbor Laboratory, New York, pp. 86–96, to obtain 47 µg of covalently closed circular DNA (ccc DNA) fraction.

After incubating the DNA fraction with *Escherichia coli* MM294 (*E. coli* MM294) which was made competent by the method described in Katsuya Shigesada, 1983, Cell Technology 2: 616–626, the *E. coli* MM294 cells were spread on an L agar plate containing 10 µg/ml of tetracycline, 50 µg/ml of streptomycin, or 30 µg/ml of chloramphenicol. The clones grown at 37° C. were taken and the plasmids in each clone were extracted by the method described in Birnboim and J. Dory, 1979, Nucleic Acid Res. 7: 1513–1523. The thus obtained plasmids were subjected to electrophoresis, and clones having a small number of bands were selected. Plasmids were extracted from the selected clones, and *E. coli* MM294 cells were re-transformed with the plasmids. Clones were reselected in accordance with the drug resistance, and plasmids were extracted from the re-selected clones. Transformation was repeated using serially diluted plasmid solutions to decrease the number of plasmids contained in a transformant. The transformation was repeated until a single plasmid was contained in the transformant. The thus obtained plasmids were designated pYU200, pYU300 and pYU400 (FIG. 1). By using the same process, pYU100 was obtained from *P. rettgeri* ATCC 9919, and pYU500 was obtained from *P. rettgeri* ATCC 29944 (FIG. 1).

The restriction maps of plasmids pYU100, pYU200, pYU300, pYU400 and pYU500 are shown in FIG. 1, and the size and the drug resistance thereof are shown in Table I. *P. rettgeri* ATCC 21118 transformed with the plasmid pYU300, i.e., *P. rettgeri* ATCC 21118 (pYU300), was deposited with Fermentation Research Institute, the accession number thereof being BP-1174.

TABLE I

| Plasmid | Length (kb) | Drug Resistance | Origin |
|---------|-------------|-----------------|--------|
| pYU100 | 7.5 | $Tc^R$ | *P. rettgeri* ATCC 9919 |
| pYU200 | 7.5 | $Tc^R$ | *P. rettgeri* ATCC 25932 |
| pYU300 | 4.2 | $Tc^R$, $Cm^R$ | *P. rettgeri* ATCC 25932 |
| pYU400 | 8.6 | $Sm^R$ | *P. rettgeri* ATCC 25932 |
| pYU500 | 7.5 | $Tc^R$ | *P. rettgeri* ATCC 29944 |

6.2. HOST RANGE

*Citrobacter freundii* IFO 12681, *Erwinia herbicola* IFO 12686, *Salmonella typhimurium* IFO 13245, *Enterobacter aerogenes* IFO 12010 and *Klebsiella pneumonia* IFO 3512 which had been made competent by the method described in Katsuya Shigesada, 1983, Cell Technology 2: 616–626, were transformed, with the plasmid pYU300 extracted from *E. coli* MM294 according to the method described in "Molecular Cloning, A Laboratory Manual," 1982, Maniatis et al., eds., Cold Spring Harbor Laboratory, New York, pp. 86–96. The transformants were cultured on L plate media. The selective pressure was applied by using chloramphenicol. The concentration of chloramphenicol differed from the species to the species and was, in the order mentioned, 15, 7.5, 15, 30 and 7.5 µg/ml, respectively. All bacteria were successfully transformed, thus demonstrating the wide host range of pYU300.

7. EXAMPLE: PRODUCTION OF L-LYSINE BY CLONING DNA CONTAINING A GENE CODING FOR DIAMINOPIMELIC ACID DECARBOXYLASE, UTILIZING THE PLASMID pYU300

The subsections below describe the shotgun cloning of *P. rettgeri* chromosomal DNA fragments into the pYU300 wide host range plasmid and the selection of recombinant plasmid, pYU303, which is believed to contain a gene coding for diaminopimelic acid decarboxylase, which is responsible for the fermentative production of L-lysine.

7.1. EXTRACTION OF CHROMOSOMAL DNA

The cells of *P. rettgeri* ATCC 21118 cultured in L-broth were lysed by the same process described in Section 6.1. Four milligrams of chromosomal DNA was obtained from the lysate by the method described in Hyuga Saito, 1966, Protein, Nucleic Acid, Enzyme Vol. 11, pp. 446–450.

7.2. DIGESTION OF DNA WITH RESTRICTION ENZYMES AND FRACTIONATION

Under the conditions according to "Advanced Bacterial Genetics, A Manual for Genetic Engineering," 1980, Davis et al., eds, Cold Spring Harbor Laboratory, New York pp. 227–230), 0.25 $\mu g/\mu l$ of the chromosomal DNA obtained in Section 7.1. above was digested with 0.12 unit/$\mu l$ of restriction enzyme HindIII for 2 hours. The digested mass (125 $\mu g$ in terms of the amount of DNA) was subjected to sucrose density gradient centrifugation (12 ml, 10–40%) and fractions of 0.5 ml each were recovered. The centrifugation was conducted using Hitachi RPS40T rotor, at 25,000 rpm for 24 hours at 20° C. The length of the DNA in each fraction was determined by electrophoresis, and the DNA fragments of 2 to 10 kb were ligated to the pYU300 plasmids having a wide host range as described below in Section 7.3. The restriction enzyme used was commercially available from Takara Shuzo Co., Ltd., Japan, and the definition of the activity unit was in accordance with that described in the accompanying manual.

7.3. PREPARATION OF VECTOR DNA

The plasmid vector pYU300 was replicated in *E. coli* MM294. Replication and extraction/purification from the cells were in accordance with "Molecular Cloning, A Laboratory Manual," 1982, Maniatis et al., eds., Cold Spring Harbor Laboratory, New York pp. 86–96. After the plasmid-containing cells cultured in L-broth containing 30 mg/l chloramphenicol were lysed with lysozyme-SDS, the DNAs were extracted by phenol extraction, and were purified by cesium chloride-ethidium bromide density gradient centrifugation and by Biogel column chromatography as described in Section 6.1. Fifty micrograms of pYU300 was obtained per one liter of medium. To make the plasmid suitable as a vector, the plasmid was completely digested with HindIII and the digested mass was treated with alkaline phosphatase in accordance with "Advanced Bacterial Genetics, A Manual for Genetic Engineering," 1980, Davis et al., eds., Cold Spring Harbor Laboratory, New York, pp. 138–139).

7.4. PREPARATION OF AUXOTROPHIC MUTANT HOSTS

*P. rettgeri* ATCC 21118 and *E. coli* MM294 cultured in 5 ml of L-broth at 37° C. for 3 hours, which were in their logarithmic phase, were subjected to mutagenesis treatment with 100 $\mu g/ml$ of nitrosoguanidine (NTG) in accordance with "Experimental Methods of Microbial Genetics," 1982, Tatsuo Ishikawa, ed., Kyoritsu Shuppan, pp. 86–88. After the treatment, lysine-auxotrophic mutants and threonine-auxotrophic mutants of each species were isolated. The mutants auxotrophic to lysine (*P. rettgeri* ATTC 21118 Lys⁻ or *E. coli* MM294 lysA) lacked the diaminopimelic acid decarboxylase activity.

7.5. LIGATION OF DNAs AND TRANSFORMATION

Based on the method described in Birnboim and J. Dory, 1979, Nucleic Acid Res. 7: 1513–1523, 10 $\mu g$ of DNA fragments obtained in Section 7.2. above and 10 $\mu g$ of vector DNAs obtained in Section 7.3. above were reacted in 100 $\mu l$ of 6 mM $MgCl_2$, 6 mM beta-mercaptoethanol, 0.5 mM ATP, 6 mM Tris-HCl (pH 6) in the presence of 0.5 units of T4 DNA ligase at 14° C. overnight. Ten microliters of the reaction mixture was mixed with 200 $\mu l$ of a suspension of lysine-auxotrophic *P. rettgeri* hosts (*P. rettgeri* ATCC 21118 Lys⁻) obtained in Section 7.4. above, which were made competent by the method described in Katsuya Shigesada, 1983, Cell Technology 2: 616–626, and the mixture was incubated at 4° C. for 45 minutes, and 42° C. for 90 seconds, and 4° C. for 1 minute. L-broth was then added to the mixture to a final volume of 1 ml, and the mixture was incubated with shaking at 37° C. for 1 hour to complete the transformation.

7.6. SCREENING TRANSFORMANTS

The transformants in the mixture prepared in Section 7.5. above were spread on a minimal medium (0.2% glucose, 0.1% ammonium sulfate, 0.2% $KH_2PO_4$, 0.7% $K_2HPO_4$, 0.01% $MgSO_4$—$7H_2O$, 0.05% sodium citrate and 20 ppm isoleucine) containing 25 $\mu g/ml$ of chloramphenicol and 1.5% agar. Selective culture was conducted by static-culturing the transformants at 37° C. Three days after, the colonies grown were transferred to the minimal medium containing chloramphenicol to confirm the viability in the presence of chloramphenicol, and then the plasmids were extracted in accordance with Birnboim and J. Dory, 1979, Nucleic Acid Res. 7: 1513–1523. The plasmids were digested with HindIII, and the digested mass was subjected to electrophoresis in order to determine the sore of the DNA fragment inserted into the recombinant plasmids. The recombinant plasmid derived from pYU300, containing an inserted 6 kb DNA fragment, was named pYU303. The restriction map thereof is shown in FIG. 2.

7.7. CONFIRMATION OF THE GENE

*P. rettgeri* ATCC 21118, *P. rettgeri* ATCC 21118 Lys⁻ (the lysine auxotroph) and *P. rettgeri* Lys⁻ (pYU303) (the lysine auxotroph transformed with pYU303) were each cultured in 5 ml of L-broth at 30° C. for 3 hours, collected by centrifugation and were washed with 25 mM Tris buffer, pH 8. The cells were then suspended in 5 mM DL-alpha, epsilon-diaminopimelic acid, 25 mM Tris buffer, pH 8, and incubated overnight at room temperature. After developing the centrifugal supernatant on a silica gel thin layer, the generation of lysine was assayed by utilizing the color development of ninhydrin to check the presence of diaminopimelic acid decarboxylase. As shown in FIG. 3, the activity of diaminopimelic acid decarboxylase was confirmed in the *P. rettgeri* transformed with pYU303.

The 6 kb HindIII fragment of pYU303, which is believed to contain the diaminopimelic acid decarboxylase gene was inserted into the HindIII site of pBR322. This recombinant plasmid was incubated with the competent cells of lysine-auxotrophic *E. coli* mutants prepared in 7.4. above to obtain a clone of which lysine-auxotrophic marker had been rescued. The plasmid obtained from this clone retransformed the lysine-auxotrophic *E. coli*. On the other hand, pYU300 did not have the re-transforming ability.

From the data presented above, it is believed that pYU303 contains a gene coding for diaminopimelic acid decarboxylase.

8. EXAMPLE: PRODUCTION OF L-THREONINE BY CLONING DNA CONTAINING A GENE RESPONSIBLE FOR THE FERMENTATIVE PRODUCTION OF L-THREONINE, UTILIZING THE PLASMID pYU300

The subsections below describe the shotgun cloning of *P. rettgeri* chromosomal DNA fragments into the pYU300 wide host range plasmid and the selection of recombinant plasmid pYU302 which contains a gene responsible for the fermentative production of L-threonine. The use of pYU302 to increase fermentative production of L-threonine is also described.

8.1. EXTRACTION OF CHROMOSOMAL DNA

The cells of *P. rettgeri* ATCC 21118 cultured in L-broth were lysed by the same process as described in Section 6.1. Four milligrams of chromosomal DNA was obtained from the lysate by the method described in Hyuga Saito, 1966, Protein, Nucleic Acid, Enzyme, Vol. 11, pp. 446–450.

8.2. DIGESTION OF DNA WITH RESTRICTION ENZYMES AND FRACTIONATION

Under the conditions according to "Advanced Bacterial Genetics, A Manual for Genetic Engineering, 1980, Davis et al., eds., Cold Spring Harbor Laboratory, New York, pp. 227–230, 0.25 μg/μl of the chromosomal DNA obtained in Section 8.2. above was digested with 0.12 unit/μl of restriction enzyme HindIII for 2 hours. The digested mass (125 μg in terms of the amount of DNA) was subjected to sucrose density gradient centrifugation (12 ml, 10–40%) and fractions of 0.5 ml each were recovered. The centrifugation was conducted using Hitachi RPS40T rotor, at 25,000 rpm for 24 hours at 20° C. The length of the DNA in each fraction was determined by electrophoresis, and the DNAs of 2 to 10 kb were ligated to the plasmids having a wide host range as described below in Section 8.4. The restriction enzyme used was commercially available from Takara Shuzo Co., Ltd., Japan, and the definition of the activity unit was in accordance with that described in the accompanying manual.

8.4. EXTRACTION, ISOLATION AND PREPARATION OF VECTOR DNA

8.4.1. EXTRACTION AND ISOLATION OF PLASMIDS

*P. rettgeri* ATCC 21118 which had been transformed with pYU300, designated *P. rettgeri* ATCC 21118 (pYU300) (FERM BP-1174), was aerobically cultured in one liter of L-broth at 37° C. for 17 hours. The pYU300 plasmid was extracted and isolated according to the procedures described in Section 6.1. as follows: the cells were suspended in 3 ml of 0.5M NaCl-0.1M EDTA-50 mM Tris-HCl (pH 8) containing 15 mg of lysozyme, and the suspension was incubated at 37° C. for 15 minutes. The suspension was frozen and then thawed and 25 ml of 0.1M Tris-HCl (pH 9), 1% SDS, 0.1M NaCl was added thereto, and the mixture was incubated at 60° C. for 20 minutes to lyse the cells. To the supernatant obtained by centrifuging the cell lysate at 30,000 rpm (100,000×g) for 30 minutes, 10 μl of 10 mg/ml RNase A was added. After incubation at 37° C. for 1 hours, the mixture was then subjected to phenol extraction and ethanol precipitation to obtain crude DNA. The crude DNA was subjected to Biogel column chromatography and cesium chloride-ethidium bromide density gradient centrifugation as described in Section 6.1. to obtain 55 μg of plasmid DNA (pYU300).

The length of the plasmid pYU300 was 4.2 kb and its drug resistance was $Tc^R$ and $Cm^R$. The restriction map of pYU300 is shown in FIG. 1.

8.4.2. PREPARATION OF VECTOR DNA

The plasmid vector pYU300 was replicated in *E. coli* MM294. Replication and extraction/purification from the cells were in accordance with "Molecular Cloning, A Laboratory Manual," 1982, Maniatis et al., eds., Cold Spring Harbor Laboratory, New York pp. 86–96. After the plasmid-containing cells cultured in L-broth containing 30 mg/l of chloramphenicol were lysed with lysozyme-SDS, the DNAs were extracted by phenol extracted and were purified by cesium chloride-ethidium bromide density gradient centrifugation and by Biogel column chromatography. Fifty micrograms of pYU300 was obtained per one liter of medium. To make the plasmid suitable as a vector, the plasmid was completely digested with HindIII and the digested mass was treated with alkaline phosphatase in accordance with "Advanced Bacterial Genetics, A Manual for Genetic Engineering," 1980, Davis et al., eds., Cold Spring Harbor Laboratory, New York, pp. 738–739.

8.5. PREPARATION OF AUXOTROPHIC HOST

*P. rettgeri* ATCC 21118 and *E. coli* MM294 cultured in 5 ml of L-broth at 37° C. for 3 hours, which were in their logarithmic phase, were subjected to mutagenesis treatment with 100 μg/ml of NTG in accordance with Experimental Methods of Microbial Genetics, 1982, Tatsuo Ishikawa, ed., pp. 86–88. After the treatment, lysine-auxotrophic mutants and threonine-auxotrophic mutants of each species were isolated. The mutants auxotrophic to threonine were designated *P. rettgeri* ATCC 21118 Thr−, or *E. coli* MM294 Thr−, respectively.

8.6. LIGATION OF DNAs AND TRANSFORMATION

Based on the method described in "Advanced Bacterial Genetics, A Manual for Genetic Engineering," 1980, Davis et al., eds., Cold Spring Harbor Laboratory, New York pp. 738–739, 10 μg of chromosomal DNA fragments obtained in Section 8.3. above and 10 μg of pYU300 vector DNAs obtained in Section 8.4. above were reacted in 100 μl of 6 mM MgCl$_2$, 6 mM beta-mercaptoethanol, 0.5 mM ATP, 6 mM Tris-HCl (pH 7.6) in the presence of 0.5 units of T4 DNA ligase at 14° C. overnight. Ten microliters of the reaction mixture was mixed with 200 μl of a suspension of *P. rettgeri* threonine-auxotrophic hosts (*P. rettgeri* ATCC 21118 Thr−) obtained in Section 8.5 above, which were made competent by the method described in Katsuya Shigesada, 1983, Cell Technology 2: 615–626, and the mixture was incubated at 4° C. for 45 minutes, and 42° C. for 90 seconds, and 4° C. for 1 minute. L-broth was then added to the mixture to a final volume of 1 ml, and the mixture was incubated with shaking at 37° C. for 1 hour to complete the transformation.

8.7. SCREENING TRANSFORMANTS

The transformants in the mixture prepared in Section 8.6. above were spread on a minimal medium plate containing 7.5 μg/ml chloramphenicol. Selective culture was conducted by static-culturing the transformants at 37° C. Three days after, the colonies grown were transferred to the minimal medium containing chloramphenicol to confirm the viability in the presence of chloramphenicol, and then the plasmids were extracted in accordance with Birnboim and Dory, 1979, Nucleic Acid Res. 7: 1513–1523. The extracted plasmids were digested with HindIII, and the digested mass was subjected to electrophoresis in order to determine the size of the DNA insert in the recombinant plasmids. The existence of two kinds of recombinant plasmids derived from pYU300, in which the direction of an inserted 8.7 kb DNA fragment was opposite to each other as shown in FIG. 4, was confirmed, and the plasmids were named pYU302 and pUY302, respectively. The transformant containing the pYU302 plasmid was designated *P. rettgeri* ATCC 21118 Thr− (pYU302).

8.8. CONFIRMATION OF THE GENE

A recombinant plasmid was prepared by inserting the 8.7 kb HindIII fragment of pYU302 into the HindIII site of pBR322 and was used to transform *E. coli* CGSC 5075, CGSC 5076 and CGSC 5077. The threonine-auxotrophic marker was rescued in each of the above strains. Therefore, it is believed that the recombinant plasmid pYU302 from *P. rettgeri* contains the genes corresponding to thrA, thrB and thrC of *E. coli*.

8.9. FERMENTATIVE PRODUCTIVITY OF THREONINE

The transformant *P. rettgeri* ATCC 21118 Thr− (pYU302) prepared in Section 8.7. above was cultured in L-broth containing 10 mg/ml of chloramphenicol. In accordance with the method described in "Molecular Cloning, A Laboratory Manual," 1982, Maniatis et al., ed. Cold Spring Harbor Laboratory, New York, pp. 86–96, 10 μg of pYU302 was obtained per 400 ml of the culture. After transforming *P. rettgeri* ATCC 21118 (i.e., the non-threonine-auxotrophic host) with the thus obtained pYU302 in the same manner as in Section 7.5., the clone which grew on the L-broth containing 10 mg/ml of chloramphenicol was isolated. Restriction analysis confirmed that the plasmid contained in the transformant was pYU302; this transformant, designated *P. rettgeri* ATCC 21118 (pYU302), was deposited with Fermentation Research Institute, and was assigned accession number FERM BP-1175.

*P. rettgeri* ATCC 21118 and *P. rettgeri* ATCC 21118 (pYU302) (FERM BP-1175) were respectively cultured in 50 ml of a medium (8% glucose, 2% ammonium sulfate, 0.1% KH$_2$PO$_4$, 0.04% MgSO$_4$—7H$_2$O, 10 ppm FeSO$_4$, 7 ppm MnCl$_2$—4H$_2$O, 50 ppm L-isoleucine, 4% CaCO$_3$, pH 7) containing 10 mg/l of chloramphenicol in 500 ml Sakaguchi flask at 30° C. for 53 hours. The threonine content in the culture media was determined by using an automatic amino acid analyzer. The threonine content in the culture medium of *P. rettgeri* ATCC 21118 was 0.20 g/l, and that of *P. rettgeri* ATCC 21118 (pYU302) (FERM BP-1175) was 0.68 g/l; thus the fermentative productivity of the latter was 3.4 times that of the former.

9. EXAMPLE: PRODUCTION OF L-THREONINE BY CLONING DNA CONTAINING A GENE RESPONSIBLE FOR THE FERMENTATIVE PRODUCTION OF L-THREONINE, USING pBR322 AND pYU300

The subsections below describe an alternative method for the construction of pYU302 and the use of this recombinant plasmid to increase the fermentative production of threonine in *P. rettgeri*.

9.1. PREPRATION OF VECTOR DNA pBR322 manufactured by Takara Shuzo Co., Ltd., was completely digested with restriction enzyme HindIII, and was treated with alkaline phosphatase in accordance with Advanced Bacterial Genetics, "A Manual for Genetic Engineering," 1980, Davis et al., eds. Cold Spring Harbor Laboratory, New York, pp. 738–739.

9.2. CLONING OF L-THREONINE GENE

DNA fragments of *P. rettgeri* ATCC 21118 chromosomal DNA digested with HindIII were ligated to the pBR322 vector prepared in Section 9.1. above, in the same manner as described in Section 8. An L-threonine-auxotrophic mutant of the host (*E. coli* MM294 Thr−) was transformed with the ligation mixture to obtain a clone of a transformant in which the L-threonine marker had been rescued. The smallest recombinant pBR322 plasmid in the transformant had a 8.7 kb foreign DNA insert.

9.3. PREPARATION OF HOST STRAIN WHICH FERMENTATIVELY PRODUCES L-THREONINE

The 8.7 kb DNA fragment obtained by HindIII digestion of the pBR322 recombinant plasmid cloned in Section 9.2. above was inserted to the HindIII site of pYU300 as in Section 8.6. to obtain a recombinant plasmid pYU302. *P. rettgeri* ATCC 21118 was transformed with the pYU302.

The *P. rettgeri* ATCC 21118 (pYU302) transformant was cultured for 48 hours in the same manner as in Section 8.9 and the fermentative productivity of L-threonine was assayed. The productivity of the transformant was 0.70 g/l, and that of non-transformed strain was 0.18 g/l; thus the productivity of transformant was 3.9 times that of the non-transformed strain.

10. EXAMPLE: PRODUCTION OF L-THREONINE BY CLONING DNA DERIVED FROM A THREONINE-ANALOG RESISTANT MUTANT

The gene complementing the auxotrophy to threonine of the host was cloned in accordance with the auxotrophy complementation method as described in Section 8, using the chromosomal DNA of a threonine analog resistant mutant, that is, an alpha-amino-beta-hydroxyvaleric acid-resistant mutant (AHV-resistant mutant) of P. rettgeri, (P. rettgeri ATCC 21118 AHV$^r$ (FERM BP-871). Chromosomal fragments of P. rettgeri ATCC 21118 AHV$^r$ (FERM BP-871) were inserted into the HindIII site of the multiple host range pYU300 vector resulting in the construction of recombinant plasmid pYU310 and pUY310. The size and the restriction map of the recombinant plasmids pYU310 and pUY310 obtained at this time are shown in FIG. 5. The direction of the inserted DNA in each of the recombinant plasmids was opposite to each other. The transformant obtained by transforming the AHV-resistant strain with pYU310 was assayed for its fermentative productivity of threonine after 45 hours culture according to the method described in Section 8.9. The threonine content of the transformant was 3.14 g/l, while that of the non-transformed strain was 2.31 g/l; thus, the productivity of threonine of the transformant was 1.4 times that of non-transformed strain.

11. DEPOSIT OF MICROORGANISMS

The following P. rettgeri strains carrying the listed plasmids have been deposited with the Fermentation Research Institute (FERM), 1-3, Higashi 1 chome Yatabe-machi Tsukuba-gun Ibaraki-ken 305, Japan, and have been assigned the following accession numbers:

| P. rettgeri Strain | Accession No. |
|---|---|
| ATCC 21118 (pYU300) | FERM BP-1174 |
| ATCC 21118 (pYU302) | FERM BP-1175 |
| ATCC 21118-AHV$^r$ | FERM BP-871 |

The present invention is not to be limited in scope by the microorganisms deposited since the deposited embodiment is intended as a single illustration of one aspect of the invention and any microorganisms which are functionally equivalent are within the scope of this invention. Indeed, various modifications of the invention in addition to those shown and described herein will become apparent to thos skilled in the art from the foregoing description and accompanying drawings. Such modifications are intended to fall within the scope of the appended claims.

It is also to be understood that all base pair sizes given for nucleotides are approximate and are used for purposes of description.

What is claimed is:

1. A wide host range plasmid pYU300 extracted from a microorganism belonging to the genus Providencia which can replicate in a second genus belonging to the family Enterobacteriaceae.

2. A recombinant plasmid comprising the wide host range plasmid pYU300 which is extracted from *Providencia rettgeri*.

3. The plasmid of claim 2, comprising the wide host range plasmid pYU300 which is extracted from *Providencia rettgeri* ATCC 25932.

4. A recombinant plasmid comprising the wide host range plasmid pYU300 extracted from a microorganism belonging to the genus Providencia which can replicate in a second genus belonging to the family Enterobacteriaceae.

5. A recombinant DNA comprising the plasmid of claim 4 containing a gene responsible for the production of L-threonine obtained from a microorganism belonging to the genus Providencia.

6. The recombinant DNA of claim 5 in which the plasmid was extracted from *Providencia rettgeri*.

7. The recombinant DNA of claim 6, comprising pYU302.

8. A transformant belonging to the genus Providencia or Escherichia, which is transformed with a recombinant DNA comprising pYU300.

9. The transformant of claim 8, in which the recombinant DNA plasmid comprises a gene responsible for the production of L-Threonine derived from a microorganism belonging to the genus Providencia, ligated to a plasmid pYU300 extracted from *Providencia rettgeri*.

10. The transformant of claim 9, wherein the recombinant DNA comprises a plasmid pYU300 containing a gene responsible for the production of L-threonine, and the transformant is a strain belonging to the genus Providencia.

11. The transformant of claim 10, in which the transformant comprises a *Providencia rettgeri* transformant.

* * * * *